(12) United States Patent
Johnson et al.

(10) Patent No.: US 8,092,515 B2
(45) Date of Patent: Jan. 10, 2012

(54) ENERGIZED STENTS AND METHODS OF USING THE SAME

(75) Inventors: Kristin D. Johnson, Louisville, CO (US); Jason Case, Longmont, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 322 days.

(21) Appl. No.: 12/412,485

(22) Filed: Mar. 27, 2009

(65) Prior Publication Data
US 2009/0254164 A1 Oct. 8, 2009

Related U.S. Application Data

(60) Provisional application No. 61/040,043, filed on Mar. 27, 2008.

(51) Int. Cl.
*A61F 2/82* (2006.01)
(52) U.S. Cl. .................................................. 623/1.15
(58) Field of Classification Search .......... 606/32, 606/34, 41; 623/1.15–1.2, 1.22, 1.34, 1.42, 623/1.44, 1.46, 23.7, 23.71
See application file for complete search history.

(56) References Cited

U.S. PATENT DOCUMENTS

| | | | |
|---|---|---|---|
| 5,125,928 A * | 6/1992 | Parins et al. ................... 606/48 |
| 5,372,600 A | 12/1994 | Beyar et al. |
| 5,840,064 A | 11/1998 | Liprie |
| 5,873,855 A | 2/1999 | Eggers et al. |
| 5,935,135 A | 8/1999 | Bramfitt et al. |
| 6,102,046 A | 8/2000 | Weinstein et al. |
| 6,179,824 B1 | 1/2001 | Eggers et al. |
| 6,350,248 B1 | 2/2002 | Knudson et al. |
| 6,387,109 B1 | 5/2002 | Davison et al. |
| 6,447,508 B1 | 9/2002 | Sharkey et al. |
| 6,582,423 B1 | 6/2003 | Thapliyal et al. |
| 2005/0278017 A1 * | 12/2005 | Gregorich ................... 623/1.44 |
| 2006/0100696 A1 * | 5/2006 | Atanasoska et al. ......... 623/1.44 |

FOREIGN PATENT DOCUMENTS
WO WO 00/16701 3/2000
* cited by examiner

*Primary Examiner* — Ryan Severson

(57) ABSTRACT

The present disclosure relates to surgical systems including energized/energizable stents, and methods of using the same in the prevention of restenosis. A surgical system for treating a stenosis and/or a restenosis site s provided. The surgical system includes an electrosurgical generator; an energy transmitting conduit connectable to the electrosurgical generator; and a stent positionable in a body lumen at a site of a stenosis. The stent is fabricated from an electrically conductive material and adapted to electrically communicate with the electrosurgical generator, and the energy transmitting conduit delivers electrosurgical energy to the site of the stenosis.

18 Claims, 9 Drawing Sheets

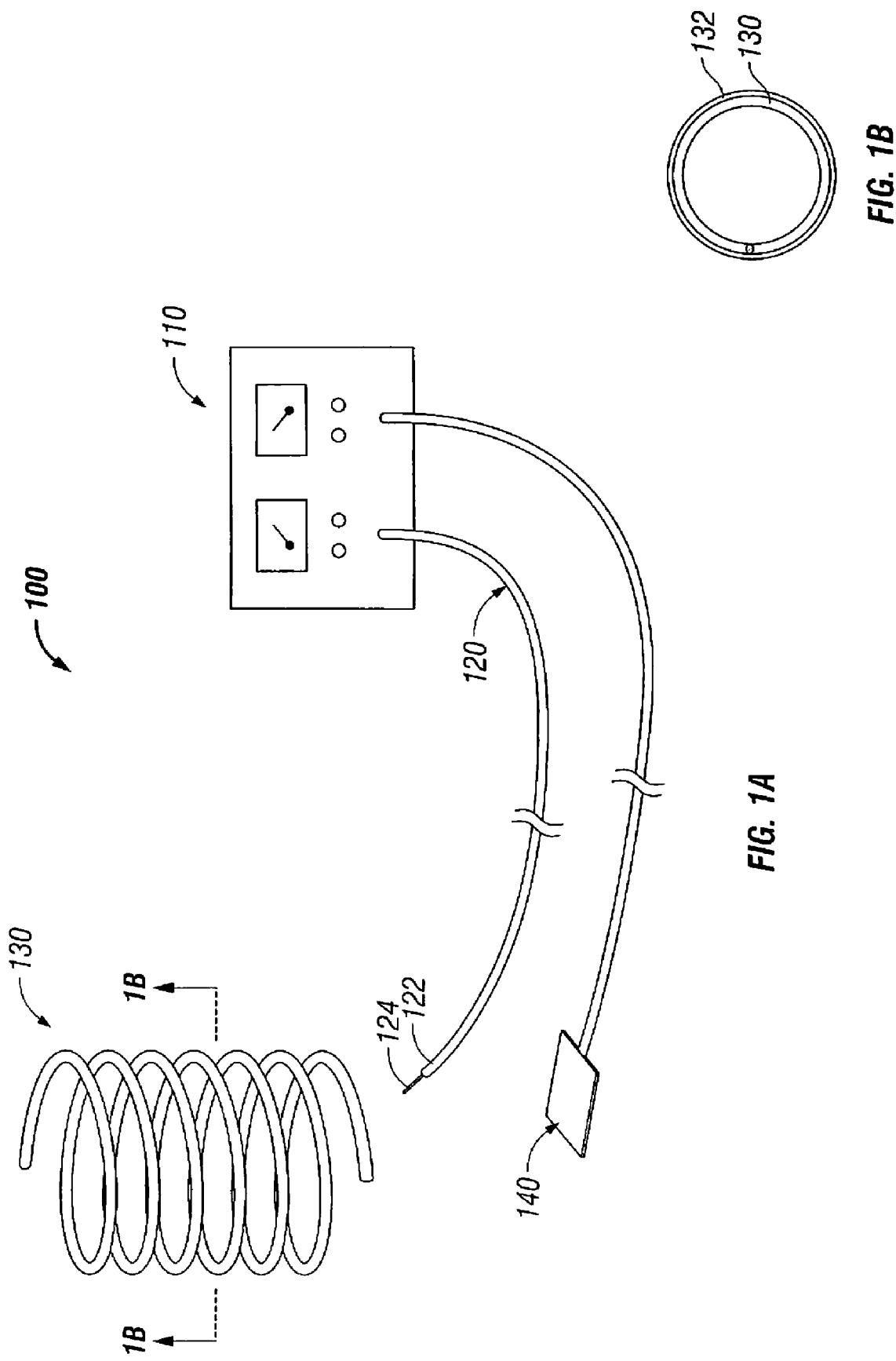

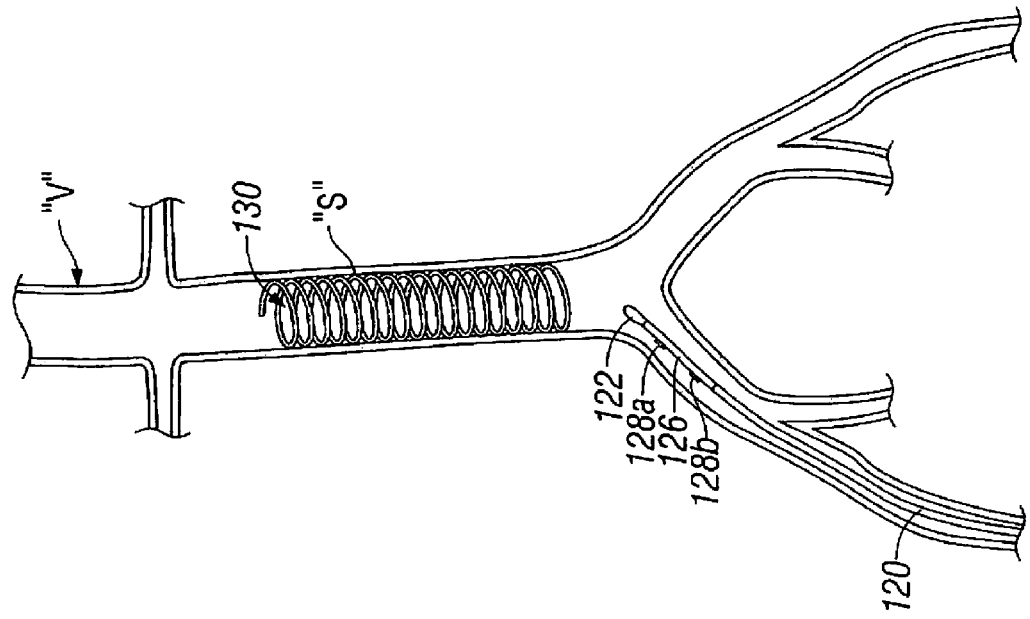
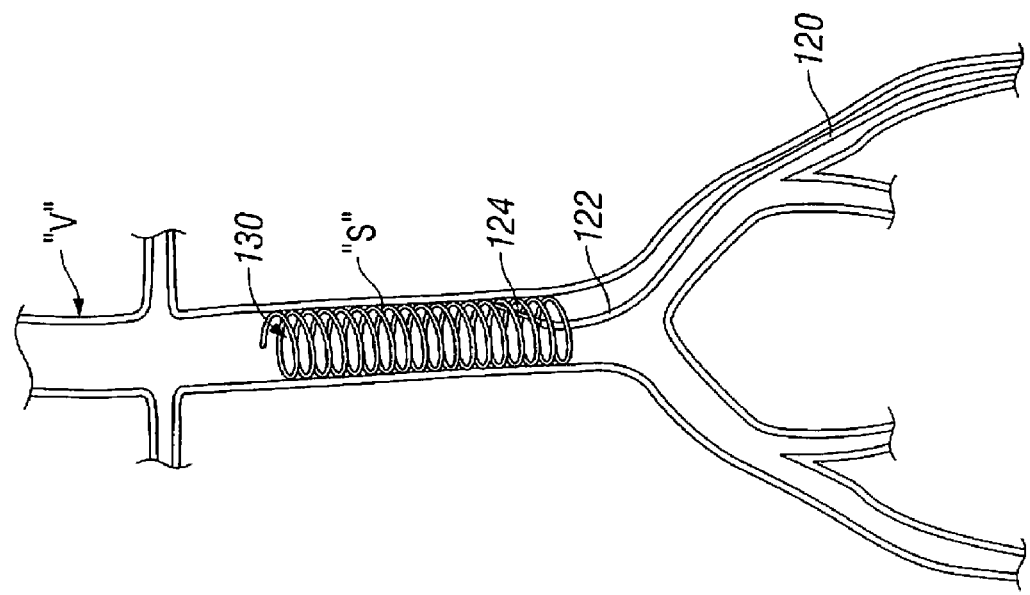

ENERGIZED STENTS AND METHODS OF USING THE SAME

CROSS-REFERENCE TO RELATED APPLICATIONS

This application claims the benefit of priority to U.S. Provisional Application Ser. No. 61/040,043 entitled "ENERGIZED STENTS AND METHODS OF USING THE SAME" filed Mar. 27, 2008 by Kristin D. Johnson et al., which is incorporated by reference herein.

BACKGROUND

1. Technical Field

The present disclosure relates to surgical systems and instruments, and methods of using the same to prevent the occurrence of restenosis and, more particularly, to surgical systems including energized/energizable stents, and methods of using the same in the prevention of restenosis.

2. Background of Related Art

Various techniques have been developed to treat many different conduits in the body when these conduits become reduced in size due to the existence of a stenosis or have been completely occluded for various reasons. With respect to the vascular pathways, angioplasty is used to open an artery or blood vessel in the region where stenosis or occlusion has occurred. A typical angioplasty procedure consists of making a small incision through the body and into a blood vessel and then maneuvering a guide wire through the vascular system to a point beyond the stenosis or occlusion. A hollow catheter with a deflatable balloon near the distal end of the guide wire is threaded over the guide wire and advanced to the point of stenosis or occlusion. The balloon is then inflated and deflated several times to widen the constricted area, and is then withdrawn from the body.

Unfortunately, although the angioplasty procedure does markedly reduce the area of stenosis or occlusion, many patients exhibit a reoccurrence of the stenosis (i.e., restenosis) within a few months of the original procedure.

Although the original stenosis occurs by means of the build up of plaque over a relatively long period of time, experimentation has lead many to believe that the reoccurrence of the stenosis after the original angioplasty procedure is unrelated to the cause of the original stenosis. It is believed that the inflation of the balloon catheter used in the angioplasty procedure causes irritation to the blood vessel. This irritation produces a mechanism of action called hyperplasia, inducing the inner layer of the blood vessel cells to rapidly reproduce, thereby causing the restenosis.

Conventionally, expandable devices, called stents, are used to maintain the inner diameter of a body lumen such as an artery. Although stents are most commonly used after angioplasty, to maintain vascular patency and help in the prevention of restenosis, stents may also be used for repair of aneurysms, stabilization of interior vessel tubes such as bronchial tubes, retention of emboli and plaque, and prevention of vessel collapse. The stents are placed at a desired location within a body lumen through a guide catheter or similar device and are expanded, by various known methods, within the lumen until they are opposed to the walls of the lumen at a preferred diameter.

Drug eluting coatings are commonly employed to reduce the irritation and/or inflammation and further reduce the possibility of restenosis. While drug eluting stents are marginally effective, such drug eluting stents have a finite period of time of drug delivery based on the rate at which the drug eluting coating is dissolved.

SUMMARY

The present disclosure relates to surgical systems including energized/energizable stents, and methods of using the same in the prevention of restenosis.

According to an aspect of the present disclosure, a surgical system for treating a stenosis and/or a restenosis site is provided. The surgical system includes an electrosurgical generator; an energy transmitting conduit connectable to the electrosurgical generator; and a stent positionable in a body lumen at a site of a stenosis. The stent is fabricated from an electrically conductive material and adapted to electrically communicate with the electrosurgical generator. The energy transmitting conduit delivers electrosurgical energy to the site of the stenosis.

The stent may be radially expandable. An outer surface of the stent may be at least partially coated with an insulative material. The stent may include a coating of a drug-eluting material on at least a portion of a surface thereof.

The energy transmitting conduit may include an insulative catheter and an electrically conductive guidewire slidably disposed within the catheter. The guidewire may be extendable from a distal tip of the catheter. The energy transmitting conduit may be flexible and may include an electrically conductive guidewire coated with an insulative material along substantially a length thereof, wherein a distal tip of the guidewire may be exposed.

The energy transmitting conduit may include a conduit having an expandable balloon provided near a distal end thereof and at least one electrical pole disposed on an outer surface of the balloon. Each electrical pole may be in electrical communication with the electrosurgical generator. The electrosurgical generator, the energy transmitting conduit and the stent may be implantable within a body.

According to another aspect of the present disclosure, a method of performing a surgical procedure to reduce the occurrence of restenosis is provided. The method includes the steps of implanting an electrically conductive stent in a body lumen at a location of a stenosis; and energizing the stent to therapeutically treat the location of the stenosis.

The method may further include the step of electrically connecting an electrosurgical generator to the implanted stent. The method may further include the step of delivering electrosurgical energy from the electrosurgical generator to the stent.

The method may still further include the steps of advancing an electrical conduit through the body lumen to the stent, said electrical conduit being in electrical communication with the electrosurgical generator; and electrically engaging the electrical conduit with the stent.

The method may include the step of delivering electrosurgical energy to the stent at a frequency of less than about six months.

The method may further include the step of advancing an expandable balloon into the stent, wherein the expandable balloon includes at least one electrical pole disposed on an outer surface thereof, and expanding the balloon to electrically engage the stent.

The method may still further include providing an insulative coating on at least a portion of an outer surface of the stent and/or providing a coating of a drug-eluting material on a surface of the stent. The method may include providing nanotubes in operative association with the stent.

BRIEF DESCRIPTION OF THE DRAWINGS

Further features and advantages of the invention will become readily apparent from the following specification and from the drawings, in which:

FIG. 1 is a schematic illustration of a surgical system for reducing the occurrence of restenosis according to an embodiment of the present disclosure;

FIG. 1A is a cross-sectional view of the stent of FIG. 1, as taken through 1A-1A thereof;

FIG. 4 is a schematic, cross-sectional illustration of the vascular system of FIG. 3 illustrating the advancement of a catheter of the surgical system through a lumen of the vascular system for interconnecting an electrosurgical generator to the stent;

FIG. 5 is a schematic, cross-sectional illustration of the vascular system of FIG. 3 illustrating the advancement of a catheter into a lumen of the vascular system, according to an alternate embodiment of the present disclosure;

DETAILED DESCRIPTION OF EMBODIMENTS

Although the present invention relates to the treatment of body conduits, lumens and the like, the present invention will be discussed with respect to a restenosis in a vascular lumen or artery.

As seen in FIG. 1, a surgical system according to an embodiment of the present disclosure is generally designated as 100. Surgical system 100 includes an electrosurgical generator 110, a catheter 120 connectable to generator 110, and an enlarged stent 130 positionable in a body lumen of a patient.

Electrosurgical generator 110 is used as a general term to describe a system capable of generating and delivering suitable therapeutic electrosurgical energy to catheter 120. Electrosurgical generator 110 may be capable of generating and delivering suitable therapeutic electrosurgical energy to a target tissue that initiates apoptosis of cells and/or rupturing of cell membranes as by ablation. The therapeutic electrosurgical energy may have a relatively high power and a relatively low pulse width. Typical power delivery may include a pulse of 1-30 nsec at less than 1 Kv in a monopolar mode and a pulse of 1-30 nsec at +/−500 volts in a bipolar mode.

Figure 7:
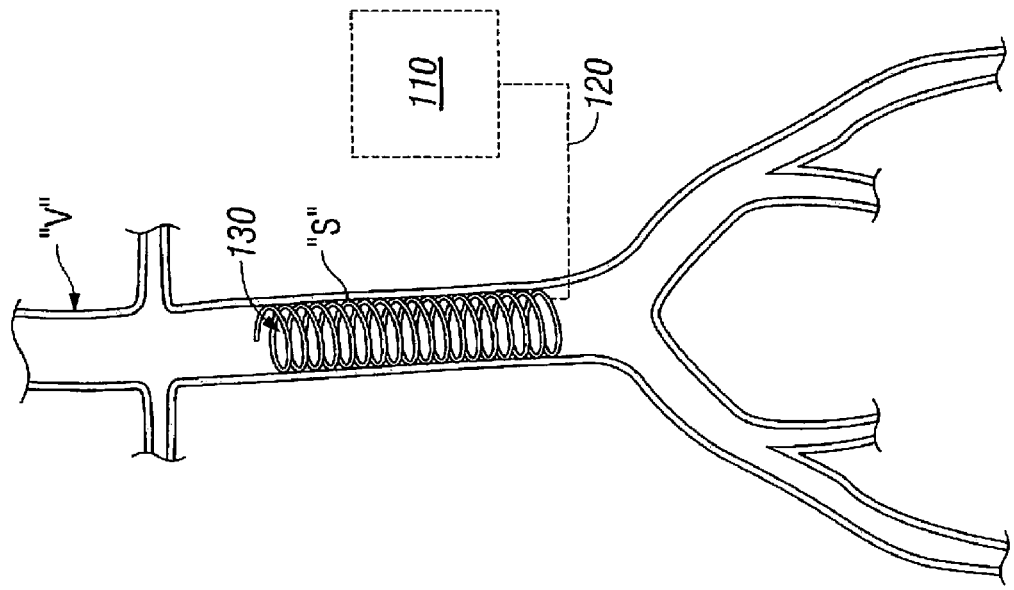
FIG. 7 is a schematic illustration of a surgical system according to another embodiment of the present disclosure implanted in a patient.

While an externally located electrosurgical generator 110 is shown in FIG. 1, electrosurgical generator 110 (or an alternate electrical energy source) may be surgically implanted within the patient, as seen in FIG. 7, as will be described in greater detail below.

In another embodiment, the alternative electrical energy source may provide the application of magnetic impulses transmitted to stent "120 after placement at the site of stenosis "S". Alternatively, the energy supplied by the alternative electrical energy source may include, but not limited to, microwave energy, radio frequency energy and ultrasonic energy.

With continued reference to FIG. 1, catheter 120 may be solid or hollow and may be fabricated from a suitable electrically conductive, flexible material, such as NITINOL or the like. An exterior surface of catheter 120 may be coated with a suitable friction reducing material, such as TEFLON (PTFE) to aid in the passage of catheter 120 through a body lumen. Additionally, catheter 120 may be coated with a suitable electrically insulative material along substantially an entire length thereof. A distal tip 122 of catheter 120 may be exposed for electrical connection with stent 130, as will be discussed in greater detail below.

Alternatively, if catheter 120 is hollow, catheter 120 may be fabricated from a suitable non-conductive material and a guidewire 124 may be slidably disposed within the lumen defined therein. Guidewire 124 is extendable or deployable from a distal tip of catheter 120. Guidewire 124 may be fabricated from a suitable electrically conductive material, such as stainless steel or the like.

With continued reference to FIG. 1, stent 130 may be fabricated from any suitable biologically inert material. In accordance with the present disclosure, it is also contemplated that at least a portion of stent 130 may be fabricated from an electrically conductive material. Examples of suitable materials for stent 130 include and are not limited to, stainless steel, NITINOL, tantalum, etc. Stent 130 may take on any shape or configuration that enables stent 130 to radially expand following positioning of stent 130 at a target surgical site.

In an embodiment, an exterior surface of stent 130 may be coated with an insulative material while an interior surface is electrically exposed. In such an embodiment, the insulative coating on the exterior of stent 130 aides in the reduction of apoptosis or in the ablation of the tissue wall while the electrically exposed inner surface of stent 130 allows for electrical connection with a guidewire 124, electrical lead, electrical contact or the like, as well as cause cell death in the more interior aspect of the lumen where plaque builds up.

In use, as will be discussed in greater detail below, stent 130 may be electrically activated, when positioned at the target site, to deliver therapeutic electrosurgical energy to the target site to reduce narrowing of the site as a result of inflammation.

As seen in FIG. 1A, stent 130 may be at least partially coated with a suitable drug-eluting material 132 that aides in the prevention of restenosis when stent 130 is placed at the target site. Examples of suitable drug-eluting materials for coating stent 130 include and are not limited to polymeric coatings comprising a polyfluoro copolymer in amounts effective to reduce thrombosis and/or restenosis when stents 130 are used. As used herein, polyfluoro copolymers means those copolymers comprising the polymerized residue of a first moiety selected from the group consisting of vinylidenefluoride and tetrafluoroethylene, the polymerized residue of a second moiety other than the first moiety and which is copolymerized with the first moiety to produce the polyfluoro copolymer, said second moiety being capable of providing toughness or elastomeric properties to the polyfluoro copolymer, wherein the relative amounts of the polymerized residue of the first moiety and the polymerized residue of the second moiety are effective to provide coatings and films made from such polyfluoro copolymers with properties effective for use in coating implantable medical devices.

In certain embodiments of the present disclosure, although not necessary, the coatings may comprise pharmaceutical or therapeutic agents in amounts effective for achieving desired purposes, e.g. for reducing thrombosis or restenosis, and stents coated with such coatings may provide sustained release of the agents. Films prepared from certain polyfluoro copolymer coatings of the present disclosure provide the physical and mechanical properties required of conventional coated medical devices, even where maximum temperatures to which the device, coatings and films are exposed are limited to relatively low temperatures, e.g. less than about 100° C., preferably at about ambient temperatures. This is particularly important when using the coating/film to deliver pharmaceutical/therapeutic agent or drugs that are heat sensitive, or when applying the coating onto temperature-sensitive devices. When maximum exposure temperature is not an issue, e.g. where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked.

The present disclosure comprises polyfluoro copolymers that provide improved biocompatible coatings for medical devices. These coatings provide inert surfaces to be in contact with body tissue of a mammal, e.g. a human, and are sufficient to reduce thrombosis, or restenosis, or other undesirable reactions. While most reported coatings made from polyfluoro homopolymers are insoluble and/or require high heat, e.g. greater than about 125° C., to obtain films with adequate physical and mechanical properties for use on implantable devices, e.g. stents, or are not particularly tough or elastomeric, films prepared from the polyfluoro copolymer coatings provide adequate adhesion, toughness or elasticity, and resistance to cracking when formed on the medical devices of the present disclosure. In certain embodiments, polyfluoro copolymers may comprise the polymerized residue of from about 65 to about 55 weight percent polymerized residue of the first moiety, e.g. VDF, and from about 35 to about 45 weight percent polymerized residue of the second moiety, e.g. hexafluoropropylene. In certain embodiments, such polyfluoro copolymers will be crystalline, although amorphous copolymers of similar composition also are employed.

The polyfluoro copolymers used for coatings may be film-forming polymers that have molecular weight high enough so as not to be waxy or tacky. The polymers and films formed therefrom should be able to adhere to the stent and not be readily deformable after deposition on the stent as to be able to be displaced by hemodynamic stresses. The polymer molecular weight should be high enough to provide sufficient toughness so that films comprising the polymers will not be rubbed off during handling or deployment of the stent. In certain embodiments the coating should not crack upon expansion of the stent.

The coatings may comprise polyfluoro copolymers, as defined hereinabove. The second moiety copolymerized with the first moiety to prepare the polyfluoro copolymer may be selected from those biocompatible monomers that would provide biocompatible polymers acceptable for implantation in a mammal, while maintaining sufficient elastomeric film properties for use on medical devices. Such monomers include, without limitation, hexafluoropropylene (HFP), tetrafluoroethylene (TFE), VDF, 1-hydropentafluoropropylene, perfluoro (methyl vinyl ether), chlorotrifluoroethylene (CTFE), pentafluoropropene, trifluoroethylene, hexafluoroacetone and hexafluoroisobutylene.

Polyfluoro copolymers may include vinylidinefluoride copolymerized with HFP, in the weight ratio of from about 50 to about 92 weight percent vinylidinefluoride to about 50 to about 8 weight percent HFP. Polyfluoro copolymers may comprise from about 50 to about 85 weight percent VDF copolymerized with from about 50 to about 15 weight percent HFP. Polyfluoro copolymers may also comprise from about 55 to about 70 weight percent VDF copolymerized with from about 45 to about 30 weight percent HFP. Polyfluoro copolymers may still also comprise from about 55 to about 65 weight percent VDF copolymerized with from about 45 to about 35 weight percent HFP. Such polyfluoro copolymers are soluble, in varying degrees, in solvents such as dimethylacetamide (DMAc), tetrahydrofuran, dimethyl formamide, dimethyl sulfoxide and n-methylpyrrolidone. Some are soluble in methylethylketone (MEK), acetone, methanol and other solvents commonly used in applying coatings to conventional implantable medical devices.

Depending on the particular device upon which the coatings and films are to be applied and the particular use/result required of the device, polyfluoro copolymers used to prepare such devices may be crystalline, semi-crystalline or amorphous.

Generally, the amount of polymer coating to be applied to the stent will vary depending on, among other possible parameters, the particular polyfluoro copolymer used to prepare the coating, the stent design and the desired effect of the coating. Generally, the coated stent will comprise from about 0.1 to about 15 weight percent of the coating, preferably from about 0.4 to about 10 weight percent. The polyfluoro copolymer coatings may be applied in one or more coating steps, depending on the amount of polyfluoro copolymer to be applied. Different polyfluoro copolymers may be used for different layers in the stent coating. In fact, in certain embodiments, it is highly advantageous to use a diluted first coating solution comprising a polyfluoro copolymer as a primer to promote adhesion of a subsequent polyfluoro copolymer coating layer that may contain pharmaceutically active materials. The individual coatings may be prepared from different polyfluoro copolymers.

The top coating can be used to delay the drug deliver of the drug contained in the first layer. Alternatively, the second layer could contain a different drug to provide for sequential drug delivery. Multiple layers of different drugs could be provided by alternating layers of first one polyfluoro copolymer, then the other. As will be readily appreciated by those skilled in the art numerous layering approaches can be used to provide the desired drug delivery.

Blends of polyfluoro copolymers also may be used to control the release rate of different agents or to provide desirable balance of coating properties, i.e. elasticity, toughness, etc., and drug delivery characteristics, e.g. release profile. Polyfluoro copolymers with different solubilities in solvents can be used to build up different polymer layers that may be used to deliver different drugs or to control the release profile of a drug. For example, polyfluoro copolymers comprising 85.5/14.5 (wt/wt) of poly (VDF/HFP) and 60.6/39.4 (wt/wt) of poly (VDF/HFP) are both soluble in DMAc. However, only the 60.6/39.4 poly (VDF/HFP) polyfluoro copolymer is soluble in methanol.

The coatings can be used to deliver therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); Angiogenic agents: vascular endothelial growth factor (VEGF), fibroblast growth factor (FGF); nitric oxide donors; cell cycle inhibitors; mTOR inhibitors; growth factor signal transduction knase inhibitors; anti-sense oligonucleotide; prodrug molecules; and combinations thereof.

Coatings may be formulated by mixing one or more therapeutic agents with the coating polyfluoro copolymers in a coating mixture. The therapeutic agent may be present as a liquid, a finely divided solid, or any other appropriate physical form. Optionally, the coating mixture may include one or more additives, e.g., nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a polyfluoro copolymer coating to modify the release profile. Appropriate relative amounts can be determined by monitoring the in vitro and/or in vivo release profiles for the therapeutic agents.

The amount of therapeutic agent will be dependent upon the particular drug employed and medical condition being treated. Typically, the amount of drug represents about 0.001% to about 70%, more typically about 0.001% to about 60%.

The quantity and type of polyfluoro copolymers employed in the coating film containing the pharmaceutic agent will vary depending on the release profile desired and the amount of drug employed. The product may contain blends of the same or different polyfluoro copolymers having different molecular weights to provide the desired release profile or consistency to a given formulation.

Polyfluoro copolymers may release dispersed drug by diffusion. This can result in prolonged delivery (over, say 1 to 2,000 hours, preferably 2 to 800 hours) of effective amounts (say, 0.001 .mu.g/cm.sup.2-min to 100 .mu.g/cm.sup.2-min) of the drug. The dosage can be tailored to the subject being treated, the severity of the affliction, the judgment of the prescribing physician, and the like.

Figure 3:
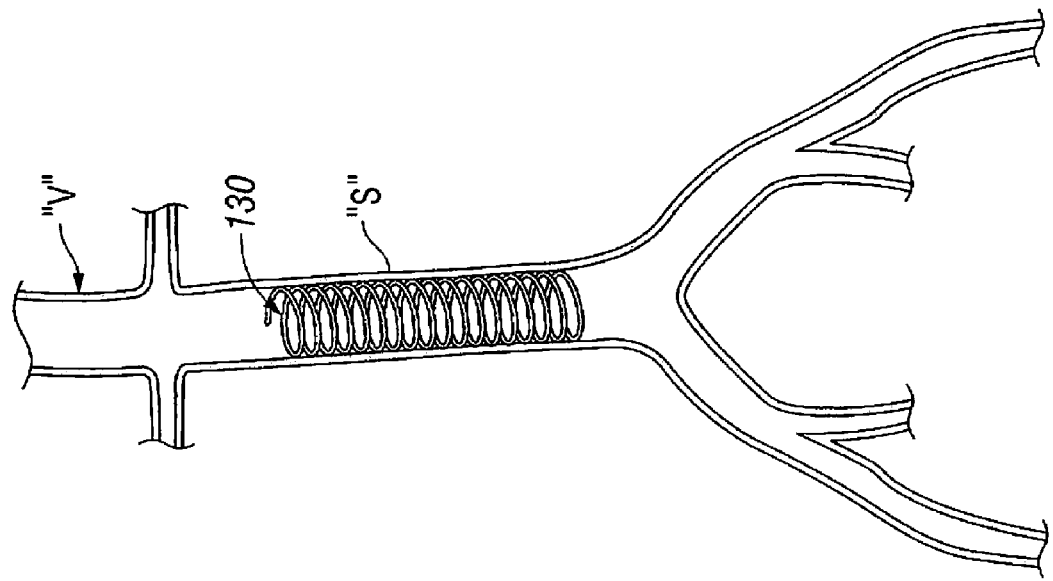
FIG. 3 is a schematic, cross-sectional illustration of the vascular system of FIG. 2 including the placement of a stent of the surgical system of FIG. 1 operatively positioned at the stenosis site.
Figure 2:
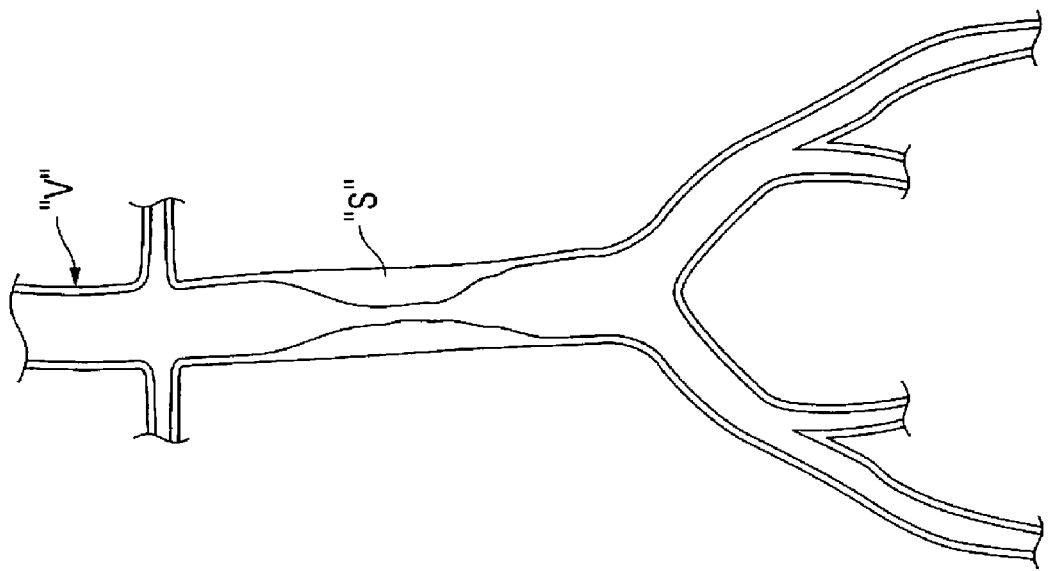
FIG. 2 is a schematic, cross-sectional illustration of a vascular system exhibiting a stenosis.

Turning now to FIGS. 2-4, a method of using surgical system 100 to treat a target site to reduce the incidence of restenosis is shown and described. As seen in FIG. 2, a vascular system "V" exhibiting a stenosis "S" is shown. As seen in FIG. 3, stenosis "S" is treated by placing stent 130, using conventional known surgical procedures, at the site of stenosis "S". The use of stent 130 functions to maintain an inner diameter of the body lumen (i.e., artery) of the vascular system "V".

As seen in FIG. 4, in order to treat the site of the stenosis "S", to prevent or reduce the occurrence of restenosis, catheter 120 is introduced into vascular system "V" and advanced to come into electrical contact with stent 130. With catheter 120 in electrical contact with stent 130, electrosurgical generator 110 is activated to transmit suitable electrosurgical energy to stent 130 and to treat the site of the stenosis "S". The electrosurgical energy delivered may be of a relatively high power and a relatively low pulse width. Voltage may range from several hundred Kv to several thousand Kv and may depend on the delivery method. For example, the voltage may be about 1 Kv in the monopolar mode and 500 volts in a bipolar mode. The pulse width of the delivered energy may range from 1-30 nsec. The electrosurgical energy delivered is suitable to initiate either apoptosis of the cells surrounding stent 130 or rupturing of the cells surrounding stent 130 that are causing the narrowing of body lumen. With electrosurgical energy being delivered to stent 130, stent 130 functions as an electrode to treat the surrounding tissue.

Alternatively, as seen in FIG. 4, with distal end 122 of catheter 120 positioned in close proximity to stent 130 or within stent 130, guidewire 124 may be advanced distally from catheter 120 to electrically engage stent 130.

It is envisioned that stent 130 may act as a first pole of an electrosurgical catheter 120. Accordingly, with guidewire 124 of catheter 120 active and in contact with stent 130, stent 130 thus becomes or is made active. Stent 130 may function as either a monopolar or a bipolar stent.

Figure 6:
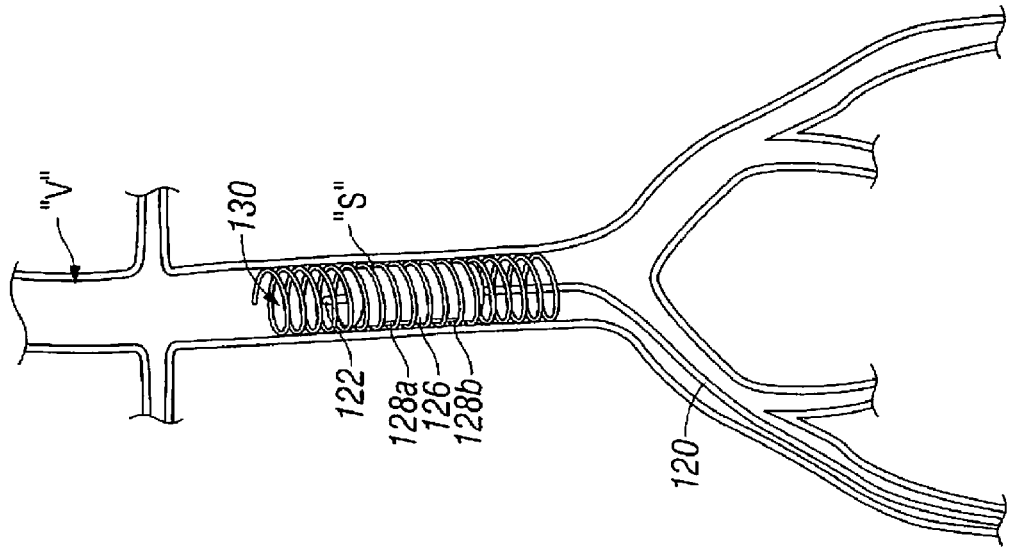
FIG. 6 is a schematic, cross-sectional illustration of the vascular system of FIG. 5 illustrating deployment of the catheter within the stent.

In one embodiment, as seen in FIGS. 5 and 6, first and second poles 128a, 128b may be disposed on an outer surface of an expandable, balloon-type device 126. Balloon-type device 126 may be supported on distal end 122 of catheter 120. In operation, as seen in FIG. 5, with balloon-type device 126 deflated, catheter 120 is advanced through vascular system "V" until balloon-type device 126 is positioned within stent 130. With balloon-type device 126 so positioned, as seen in FIG. 6, balloon-type device 126 is expanded to engage poles 128a, 128b thereof with stent 130.

It is contemplated that if the original stent 130 includes a coating 132 of drug-eluting materials thereon (see FIG. 1A), when implanted, that electrical activation of stent 130 may not be necessary until sometime after the drug-eluting material has dissolved into the body.

Turning now to FIG. 7, surgical system 100 may be completely implanted within the body of a patient and thus further invasive procedures will not be necessary in order to activate stent 130 over time. Electrosurgical generator 110 may include a microprocessor for determining when activation of electrosurgical generator 110 is to take place and the level of power to be delivered. An electrical conduit 120 is implanted within the body and extends between electrosurgical generator 110 and stent 130.

Timing of the delivery of electrosurgical energy to stent 130 may be determined by the rate of cell regeneration at the site of the stenosis. Since restenosis commonly occurs within approximately six (6) months of stent placement, delivery of electrosurgical energy to stent 130 may take place with a frequency of less than about 6 months.

Electrosurgical energy delivery may be monopolar, bi-polar or multi-polar. In a monopolar mode energy is delivered from the electrosurgical generator 110 to the stent 130 and electrosurgical currents, are returned via a ground, the chassis of the electrosurgical generator or a return/grounding pad electrode (not explicitly shown) in contact with the patient. In a bi-polar mode energy is delivered between two electrodes and in a multi-polar mode energy is delivered between two or more electrodes and a common pole, or electrode.

Surgical system 100 may include the various embodiments disclosed herein. For example, electrical conduit 120 may be a potential catheter 260 as disclosed hereinbelow or other suitable means of delivering energy to a stent known in the art. Stent 130 may be a stent as disclosed herein or any other suitable stent know in the art.

Figure 8A:
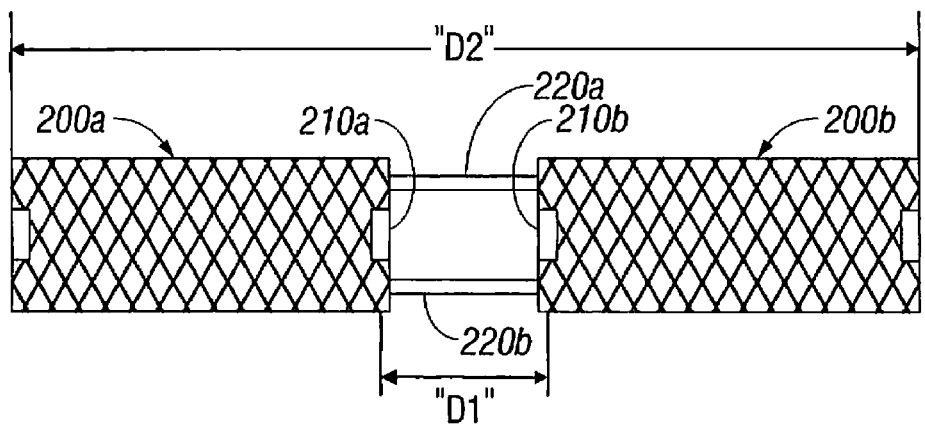
FIG. 8A is a schematic illustration of a multi-portion stent according to another embodiment of the present disclosure.

In one embodiment, as illustrated in FIG. 8A, a stent 230 includes two or more electrically isolated portions 200a, 200b each including at least one stent electrode 210a, 210b. Stent electrodes 210a, 210b are electrically connected to the various strands of the respective portions 200a, 200b. Electrically isolated portions 200a, 200b may be discrete portions or may be connected by one or more positioning members 220a, 220b configured to position portions 200a, 200b a fixed distance "D1" relative to each other.

Figure 8B:
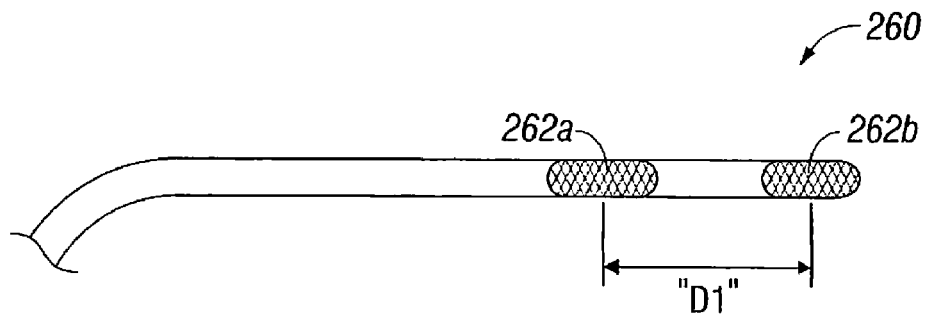
FIG. 8B is a schematic illustration of a distal tip of a potential catheter according to another embodiment of the present disclosure.
Figure 8C:
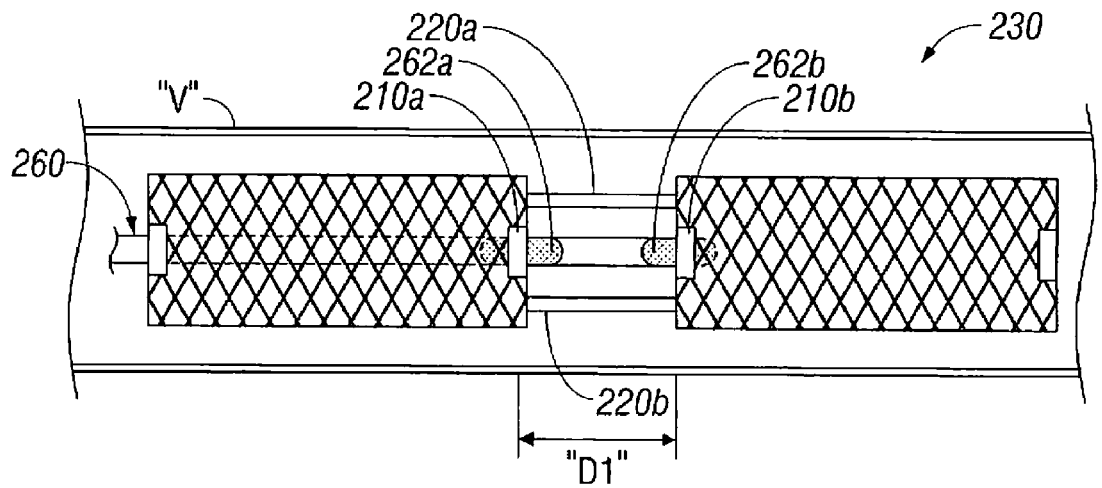
FIG. 8C is a schematic illustration of the multi-portion stent of FIG. 8A and the potential catheter of FIG. 8B in use.

A potential catheter 260, as illustrated in FIG. 8B, includes at least two catheter electrodes 262a, 262b positioned proximate a distal end thereof. Potential catheter 260 is configured to be inserted into the vascular system to access stent 230. Catheter electrodes 262a, 262b are spaced a distance "D1" from one another such that when potential catheter 260 is positioned adjacent stent 230, as illustrated in FIG. 8C, catheter electrodes 262a, 262b are positioned adjacent respective stent electrodes 210a, 210b of the stent 230. Electrosurgical energy is delivered to stent 230 by catheter electrodes 262a, 262b of the potential catheter 260 when in a bi-polar mode and thus electrosurgical energy is conducted between portions 200a, 200b of stent "S".

Catheter electrodes 262a, 262b and/or stent electrodes 210a, 210b may include a securing means (not explicitly shown) for securing potential catheter 260 to stent 230 and/or for facilitating contact between catheter electrodes 262a, 262b and stent electrodes 210a, 210b. Suitable securing means may include and are not limited to magnetic attachment means, mechanical attachment means, such as, for example, a slip-lock connector, a keyhole locking connector, a clip connector, a hook connector, or combination thereof, or any other suitable connector. Alternatively, securing means may be a separate device, such as, for example, an inflatable balloon that presses the catheter electrodes 262a, 262b into contact with the respective stent electrodes 210a, 210b.

In use, as illustrated in FIG. 8C, stent 230 is positioned and/or secured in vessel "V". The step of positioning and/or securing the stent 230 may occur during the current surgical procedure or stent 230 may have been positioned in vessel "V" during a prior surgical procedure. Potential catheter 260 is introduced into vessel "V" and catheter electrodes 262a, 262b are positioned adjacent to and in contact with the respective stent electrodes 210a, 210b of stents 200a, 200b. The electrosurgical generator then delivers the desired therapeutic electrical energy to stent 230 and/or performs diagnostic/condition measurements.

The electrosurgical generator (not explicitly shown) may sense at least one characteristic related to stent 230, such as, for example, electrode contact quality or tissue impedance. Electrosurgical energy may be delivered as a single continuous application or may be delivered as a series of energy pulses. The electrosurgical generator may sense or measure a characteristic before, during or after the delivery of electrosurgical energy.

Figure 9A:
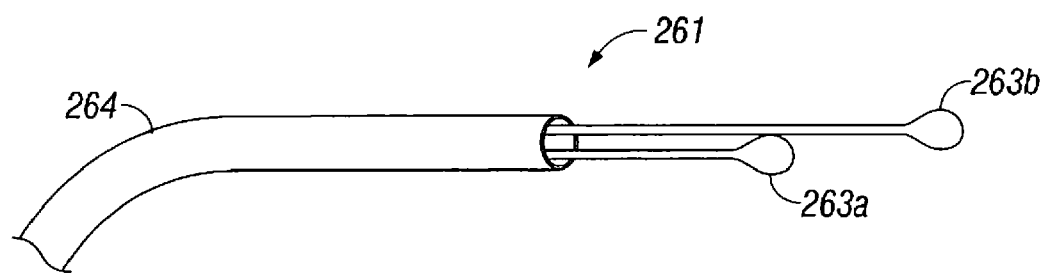
FIG. 9A is a schematic illustration of a distal tip of a potential catheter with deployable catheter electrodes according to another embodiment of the present disclosure.

In yet another embodiment, as illustrated in FIG. 9A, potential catheter 261 includes a catheter body 264 and one or more independently deployable catheter electrodes 263a, 263b. In a first condition, catheter electrodes 263a, 263b are substantially contained within catheter body 264. In a second condition, at least one of the catheter electrodes 263a, 263b are deployed distally from the catheter body 264. Potential catheter 261, while in a first condition, is configured to be inserted into the vascular system and positioned relative to a stent as illustrated and discussed hereinbelow.

Figure 9B:
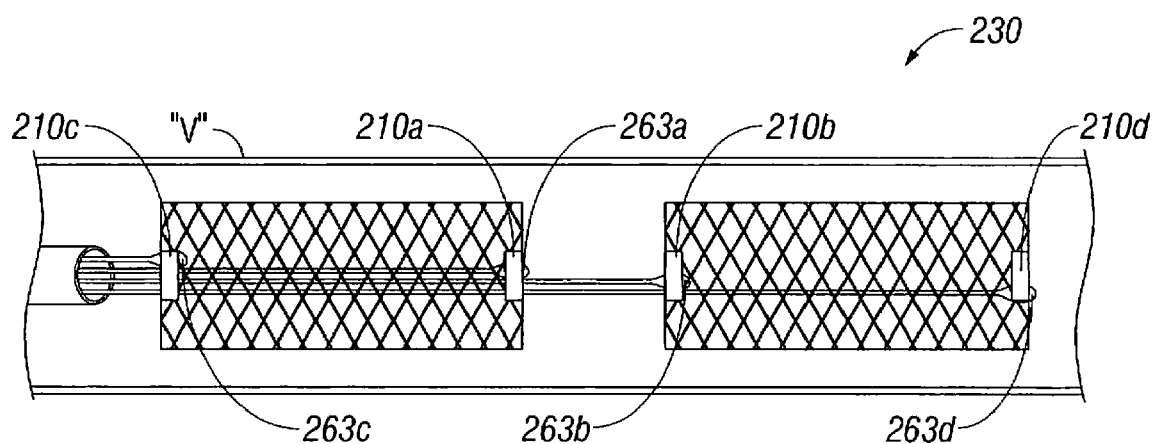
FIG. 9B is a schematic illustration of a variation of the multi-portion stent of FIG. 8A and a variation of the deployable potential catheter of FIG. 9A according to another embodiment of the present disclosure.

In use, catheter 261 is positioned in a vessel, adjacent to a stent, while configured in a first, retracted condition, as shown in FIG. 9A. Alternatively, catheter electrodes may further retract and be fully contained within catheter body 264. As illustrated in FIG. 9B, catheter electrodes 263a-263d are subsequently deployed to a second condition in order to operatively engage the stent.

Catheter electrodes 263a-263d deploy from catheter body 264 of potential catheter 261 and are positioned adjacent each respective stent electrode 210a-210d. The deployed distance for each catheter electrode 263a-263d may be individually adjusted; therefore, the position of each stent portion 200a, 200b, relative to each other, need not be fixed by any positioning members similar to positioning members 220a, 220b illustrated in FIGS. 8A and 8C.

As seen in FIG. 9B, stent 230 includes two electrically isolated portions 200a, 200b each including two stent electrodes 210a, 210c and 210b, 210d, respectively. Stent electrodes 210a, 210c are electrically connected to a portion of the strands that form the first portion 200 and stent electrodes 210b, 210d are electrically connected to a portion of the electrical strands that form the second portion 200b. Electrodes pairs 210a, 210c and 210b, 210d in first and second portions 200a, 200b, respectively, are electrically isolated from each other, forming a multi-polar stent with four electrically isolated stent electrodes 210a-210d. Electrosurgical energy may be directed between two or more of the stent electrodes.

Isolation of the electrode pairs 210a, 210b and 210b, 210d may be accomplished by physically separating the strands forming the stent 230 or by selectively insulating the strands where they cross or intersect. Means of insulating may be a suitable insulating coating or a suitable insulating material.

Catheter 261 may include catheter electrodes 263a-263d configured to connect to respective stent electrodes 210a-210d and to the electrosurgical generator (not explicitly shown) in order to perform the desired therapeutic procedure, operation, measurement or combination thereof.

Electrosurgical generator may deliver energy in a bi-polar mode and/or a multi-polar mode. In a bi-polar mode energy may be selectively delivery between any two of the four stent electrodes 210a-210d. In a multi-polar mode, one stent electrode, e.g., stent electrode 210a, may be selected as a first pole, or common electrode, and at least two of the remaining three stent electrodes 210b-210d may be selected as a second pole, or supply electrodes. Stent electrodes 210a-d may be arranged in other suitable energy delivery arrangements and configurations that utilize three or more electrodes.

Figure 10A:
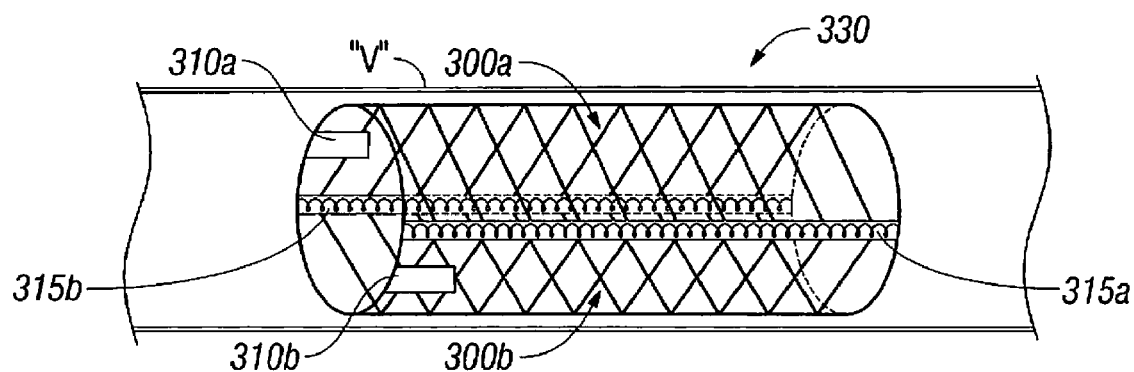
FIG. 10A is a multi-portion stent according to another embodiment of the present disclosure.

In yet another embodiment, stent 330, as illustrated in FIG. 10A, is divided longitudinally such that stent 330 forms at least two electrically isolated portions 300a, 300b each including at least one stent electrode 310a, 310b. Stent electrodes 310a, 310b are electrically connected to the various strands of the respective portions 300a, 300b. Electrically isolated portions 300a, 300b may be connected to one another by an insulating or dielectric strip 315a, 315b, by one or more positioning members, as illustrated in FIGS. 8A and 8C, or by any other suitable means to electrically isolate the two portions 300a, 300b from one another.

Figure 10B:
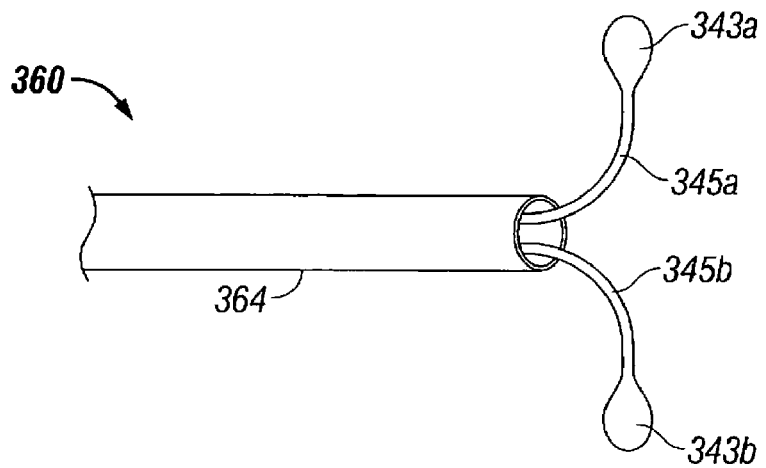
FIG. 10B is a schematic illustration of the distal tip of a potential catheter with arcuately deployable catheter electrodes.

As seen in FIG. 10B, a potential catheter, according to another embodiment of the disclosure, is shown as 360. Potential catheter 360 includes a catheter body 364 and one or more deployable catheter electrodes 343a, 343b. In a first condition, catheter electrodes 343a, 343b are substantially contained within a catheter body 364. In a second condition, at least one of the catheter electrodes 343a, 343b are deployed distally from catheter body 364. Potential catheter 360, while in a first condition, is configured to be inserted into the vascular system and positioned relative to a stent as illustrated and discussed hereinbelow.

Catheter electrodes 343a, 343b may deploy arcuately or curvilinearly from a longitudinal axis of the catheter body 364. Catheter electrodes 343a, 343b attach to, or are formed from, the distal portion of elongate conductors 345a, 345b. Elongate conductors 345a, 345b may include suitable shape memory materials and may form a predetermined shape when not constricted within the catheter body 364.

Figure 10C:
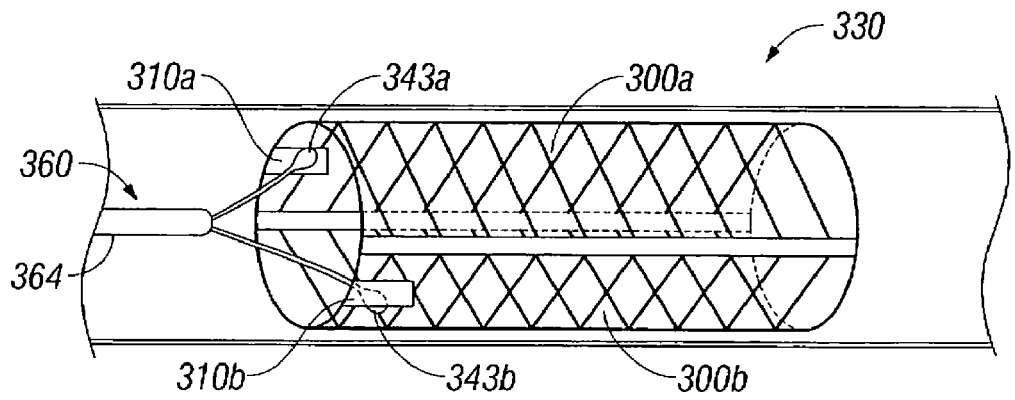
FIG. 10C is a schematic illustration of the multi-portion stent of FIG. 10A and the potential catheter of FIG. 10B shown in use.

FIG. 10C illustrates the potential catheter 360 from FIG. 10B operatively connected to stent 330 to provide electrosurgical energy to stent 330. Potential catheter 360 may deliver energy in a bi-polar mode wherein the electrosurgical energy is conducted between the two portions 300a, 300b of stent 330.

The electrosurgical current traveling between the two portions 300a, 300b of stent 360 may travel along the surface of the vessel and may dislodge plaque emboli or other materials from the surface of stent 330 and/or materials on the surface of vessel "V".

Figure 11A:
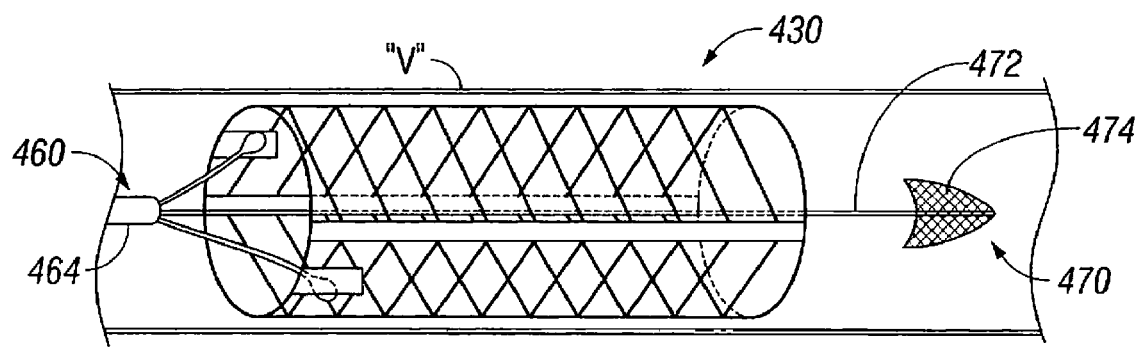
FIG. 11A is a schematic illustration of the multi-portion stent of FIG. 10A and a variation of the potential catheter of FIG. 10B including a filter in an undeployed condition.

FIG. 11A illustrates a potential catheter 460, similar to the potential catheter 360 from FIGS. 10A and 10B, including a filter 470 to catch materials dislodged from the vessel "V" or stent 430. In a first condition filter 470 may retract to, or at least partially retract within, catheter body 464. Filter 470 may attach to a distal end of catheter body 464 and form a rounded or pointed tip or configuration to assist in positioning potential catheter 460 within a vascular system.

In a second condition filter 470 is extended away from catheter body 464 by filter feedline 472. Filter 470 may be positioned in the vessel "V" down stream from stent 430 by further extending filter feedline 472. Positioning of filter 470 is performed with filter 470 in an undeployed condition with filter mesh 474 positioned adjacent filter feedline 472. In an undeployed condition, filter 470 may pass through and beyond stent 430.

Figure 11B:
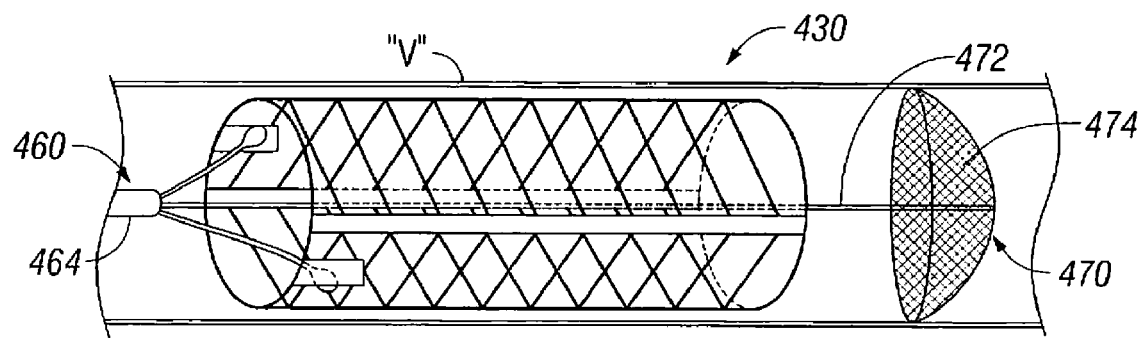
FIG. 11B is a schematic illustration of the multi-portion stent of FIG. 10A and the potential catheter of FIG. 11A with the filter in a deployed condition.

After positioning filter 470 in vessel "V", filter 470 may be deployed, as illustrated in FIG. 11B. Filter 470 may deploy and form an umbrella-shaped structure or other suitable structure that provides a pocketed area to catch and hold debris dislodge from vessel "V" or stent 430.

Filter 470 may close to an undeployed condition after delivery of electrosurgical energy thereby containing the debris collected in the filter mesh 474. Filter 470 may be retracted to a first condition wherein filter 470 is retracted to, or at least partially retract within, catheter body 464. Potential catheter 460, along with the debris collected in the filter mesh, may then be removed from the vascular system.

It is envisioned that nanotubes may be placed on the surface of any of the stents disclosed herein in order to create conductive and non-conductive regions on the surface of the stent. As used herein, nanotubes are conductive materials known for their unique physical properties in that they may be applied as thin coatings. Metallic nanotubes may provide an electric current density more than 100 times greater than metals such as silver or copper, may increase the strength of the stent by as much as several to many times that of steel while reducing the occurrence of strain failures.

Application and/or placement of nanotubes may inhibit growth of undesirable cells, such as, for example, plaque emboli or undesirable bacteria. For example, coating at least a portion of the strand surface may inhibit growth of cells on the coating and/or the adjacent surfaces of the strands of the stent. Alternatively, application and/or placement of nanotubes on a stent may be arranged to provide optimal electrosurgical energy delivery to target cells while minimizing electrosurgical energy delivery to unintended cells.

Figure 12A:
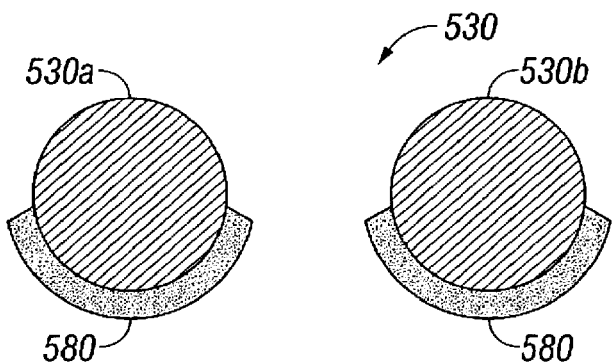
FIGS. 12A-12D are transverse cross-sectional views of a portion of a stent with nanotube coatings thereon.

FIGS. 12A-12D each illustrate a cross-section of two strands 530a, 530b of a stent 530 with a coating of nanotubes. In FIG. 12A, nanotubes 580 are selectively applied to at least a portion of the outer surface (e.g., a partial circumference) of the strands 530a, 530b of the stent 530. Nanotubes 580 may coat the outer surface, placing the nanotubes 580 in contact with the vessel, the inner surface or any suitable portion of the strands 530a, 530b. Coating of nanotubes 580 may be uniform across the length of the strands 530a, 530b or non-uniform.

Figure 12B:
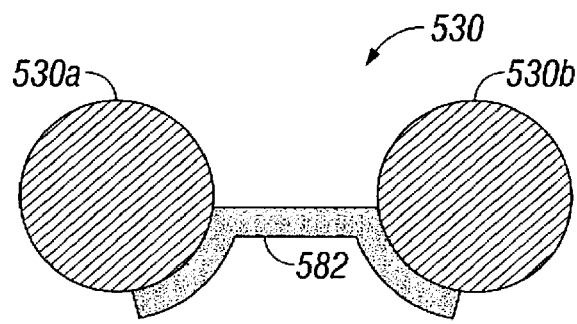
Figure 12C:
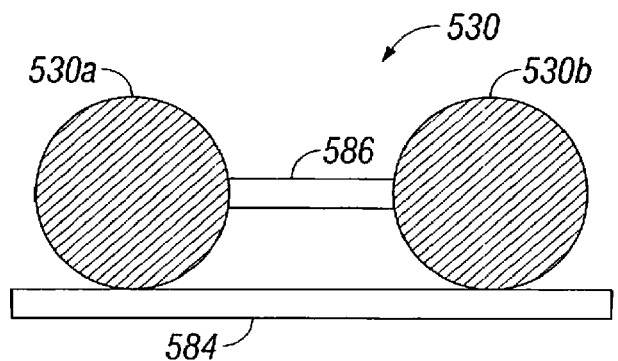
Figure 12D:
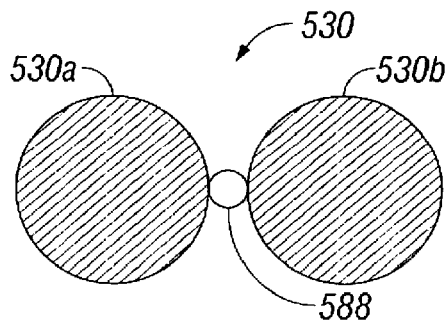

In FIGS. 12B-12D, nanotubes 582, 584, 586 are placed between two adjacent spirals of the stent 530. In FIG. 12B, nanotubes 582 coat at least a portion of strands 530a, 530b of the stent 530 and form a connection between at least two strands 530a, 530b of the stent 530.

In FIG. 12C, nanotubes 584, 586 are substantially perpendicular to strands 530a, 530b and may interconnect two or more strands 530a, 530b of the stent 530. Nanotube 584 may contact the outer (or inner) surface of strands 530a, 530b. In the alternative, nanotubes 586 may be positioned between strands 530a, 530b.

In FIG. 12D, nanotubes 588 are substantially parallel and positioned between strands 530a, 530b in at least a portion of the stent 530 or nanotubes 588 may separate the strands 530a, 530b throughout a majority of stent 530.

The foregoing description is merely a disclosure of particular embodiments and is no way intended to limit the scope of the invention. Other possible modifications are apparent to those skilled in the art and all modifications are to be defined by the following claims.

What is claimed is:

1. A surgical system for treating a stenosis and/or a restenosis site, the surgical system comprising:
    an electrosurgical generator;
    an energy transmitting conduit connectable to the electrosurgical generator; and
    a monopolar stent positionable in a body lumen at a site of a stenosis, wherein the stent is fabricated from an electrically conductive material and adapted to electrically communicate with the electrosurgical generator, and the energy transmitting conduit delivers electrosurgical energy to the site of the stenosis; and
    a return pad operatively coupled to the electrosurgical generator and configured to return the electrosurgical energy to the electrosurgical generator.

2. The surgical system according to claim 1, wherein the stent is radially expandable.

3. The surgical system according to claim 1, wherein an outer surface of the stent is at least partially coated with an insulative material.

4. The surgical system according to claim 1, wherein the energy transmitting conduit includes an insulative catheter and an electrically conductive guidewire slidably disposed within the catheter.

5. The surgical system according to claim 4, wherein a guidewire is extendable from a distal tip of the catheter.

6. The surgical system according to claim 1, wherein the energy transmitting conduit is flexible and includes an electrically conductive guidewire coated with an insulative material along substantially a length thereof, wherein a distal tip of the guidewire is exposed.

7. The surgical system according to claim 1, wherein the energy transmitting conduit includes a conduit having an expandable balloon provided near a distal end thereof and at least one electrical pole disposed on an outer surface of the balloon, wherein each electrical pole is in electrical communication with the electrosurgical generator.

8. The surgical system according to claim 1, wherein the electrosurgical generator, the energy transmitting conduit and the stent are implantable within a body.

9. The surgical system according to claim 1, wherein the stent includes a coating of a drug-eluting material on at least a portion of a surface thereof.

10. A method of performing a surgical procedure to reduce the occurrence of restenosis, comprising the steps of:
    positioning a return pad on a patient;
    implanting an electrically conductive monopolar stent in a body lumen at a location of a stenosis;
    energizing the stent with electrosurgical energy to therapeutically treat the location of the stenosis and returning the electrosurgical energy through the return pad.

11. The method according to claim 10, further comprising the step of electrically connecting an electrosurgical generator to the implanted stent.

12. The method according to claim 11, further comprising the step of delivering electrosurgical energy from the electrosurgical generator to the stent.

13. The method according to claim 11, further comprising the steps of:
    advancing an electrical conduit through the body lumen to the stent, said electrical conduit being in electrical communication with the electrosurgical generator; and
    electrically engaging the electrical conduit with the stent.

14. The method according to claim 10, further comprising the step of delivering electrosurgical energy to the stent at a frequency of less than about once every six months.

15. The method according to claim 10, further comprising the step of advancing an expandable balloon into the stent, wherein the expandable balloon includes at least one electrical pole disposed on an outer surface thereof, and expanding the balloon to electrically engage the stent.

16. The method according to claim 10, further comprising providing an insulative coating on at least a portion of an outer surface of the stent.

17. The method according to claim 10, further comprising the step of providing a coating of a drug-eluting material on a surface of the stent.

18. The method according to claim 10, further comprising providing nanotubes in operative association with the stent.

* * * * *